(12) United States Patent
Igarashi et al.

(10) Patent No.: US 9,820,637 B2
(45) Date of Patent: Nov. 21, 2017

(54) IMAGE PICKUP APPARATUS AND ENDOSCOPE INCLUDING IMAGE PICKUP APPARATUS

(71) Applicant: OLYMPUS CORPORATION, Tokyo (JP)

(72) Inventors: Takatoshi Igarashi, Ina (JP); Noriyuki Fujimori, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/666,699

(22) Filed: Mar. 24, 2015

(65) Prior Publication Data

US 2015/0190040 A1   Jul. 9, 2015

Related U.S. Application Data

(63) Continuation of application No. PCT/JP2013/063301, filed on May 13, 2013.

(30) Foreign Application Priority Data

Sep. 24, 2012  (JP) .................................. 2012-209817

(51) Int. Cl.
*A61B 1/05* (2006.01)
*H01L 31/0203* (2014.01)
*H01L 27/146* (2006.01)

(52) U.S. Cl.
CPC ........ *A61B 1/051* (2013.01); *H01L 27/14618* (2013.01); *H01L 27/14636* (2013.01); *H01L 31/0203* (2013.01); *H01L 2224/13* (2013.01)

(58) Field of Classification Search
CPC .............. A61B 1/051; H01L 27/14636; H01L 27/14618; H01L 31/0203
See application file for complete search history.

(56) References Cited

U.S. PATENT DOCUMENTS

| 2004/0041247 | A1 | 3/2004 | Kinsman |
| 2004/0069998 | A1* | 4/2004 | Harazono ......... H01L 27/14618 257/81 |

(Continued)

FOREIGN PATENT DOCUMENTS

| EP | 2164098 A1 | 3/2010 |
| JP | 2005-005488 A | 1/2005 |

(Continued)

OTHER PUBLICATIONS

International Search Report dated Jul. 23, 2013 issued in PCT/JP2013/063301.

(Continued)

*Primary Examiner* — Peniel M Gumedzoe
(74) *Attorney, Agent, or Firm* — Scully, Scott, Murphy & Presser, P.C.

(57) ABSTRACT

An image pickup apparatus includes a substrate, on a first surface of which a light receiving section and a peripheral circuit section are formed, a multilayer wiring layer stacked on the first surface and including a plurality of metal layers and insulating layers, a translucent cover located on the multilayer wiring layer, and a side surface sealing member which extends from a peripheral section of a surface in the translucent cover to the substrate side while having a frame shape, and protects outer peripheral side surfaces of the multilayer wiring layer.

11 Claims, 9 Drawing Sheets

(56) References Cited

U.S. PATENT DOCUMENTS

| | | | |
|---|---|---|---|
| 2005/0167707 A1* | 8/2005 | Funaki | H01L 27/14603 257/291 |
| 2006/0035415 A1* | 2/2006 | Wood | H01L 27/14618 438/125 |
| 2006/0138480 A1 | 6/2006 | Adkisson et al. | |
| 2006/0154034 A1* | 7/2006 | Araki | H01L 27/14632 428/209 |
| 2007/0267743 A1 | 11/2007 | Mizusawa et al. | |
| 2008/0042227 A1 | 2/2008 | Asano et al. | |
| 2008/0108170 A1 | 5/2008 | Adkisson et al. | |
| 2008/0191334 A1 | 8/2008 | Lee et al. | |
| 2009/0059055 A1 | 3/2009 | Nakano et al. | |
| 2009/0065821 A1* | 3/2009 | Lee | H01L 27/14621 257/292 |
| 2009/0189233 A1* | 7/2009 | Liu | H01L 27/14625 257/432 |
| 2010/0091168 A1 | 4/2010 | Igarashi et al. | |
| 2010/0102437 A1 | 4/2010 | Suto | |
| 2011/0068476 A1 | 3/2011 | Kawasaki et al. | |

FOREIGN PATENT DOCUMENTS

| | | |
|---|---|---|
| JP | 2007-123351 A | 5/2007 |
| JP | 2007-288024 A | 11/2007 |
| JP | 2007-335830 A | 12/2007 |
| JP | 2008-526022 A | 7/2008 |
| JP | 2009-064839 A | 3/2009 |
| JP | 2009-206496 A | 9/2009 |
| JP | 2009-212271 A | 9/2009 |
| JP | 2010-098066 A | 4/2010 |
| JP | 2010-219402 A | 9/2010 |
| JP | 2011-071239 A | 4/2011 |
| JP | 2012-015470 A | 1/2012 |
| WO | 99/18613 A1 | 4/1999 |
| WO | WO 2006071540 A2 | 7/2006 |
| WO | WO 2006073085 A1 | 7/2006 |
| WO | WO 2009/005017 A1 | 1/2009 |

OTHER PUBLICATIONS

Extended Supplementary European Search Report dated Apr. 6, 2016 from related European Application No. 13 83 8843.4.

* cited by examiner

IMAGE PICKUP APPARATUS AND ENDOSCOPE INCLUDING IMAGE PICKUP APPARATUS

CROSS REFERENCE TO RELATED APPLICATION

This application is a continuation application of PCT/JP2013/063301 filed on May 13, 2013 and claims benefit of Japanese Application No. 2012-209817 filed in Japan on Sep. 24, 2012, the entire contents of which are incorporated herein by this reference.

BACKGROUND OF INVENTION

1. Field of the Invention

The present invention relates to an image pickup apparatus in which a multilayer wiring layer including a plurality of metal layers and insulating layers for insulating the metal layers is stacked on a substrate and a translucent cover is located on the multilayer wiring layer, and an endoscope including the image pickup apparatus.

2. Description of the Related Art

Conventionally, an electronic endoscope, a camera-equipped cellular phone, a digital camera, and the like including image pickup apparatuses provided with image pickup devices such as a CCD and a CMOS are well known.

In recent years, in the image pickup apparatuses, an image pickup apparatus of a wafer level chip size package (hereinafter referred to as WL-CSP) type is well known.

As a technique for completing packaging of a plurality of image pickup apparatuses using the WL-CSP, a manufacturing method explained below is known. First, a translucent cover glass wafer is stuck in a wafer level on a multilayer wiring layer of an image sensor wafer, on which a plurality of image pickup devices are formed, including a multilayer wiring layer including a plurality of metal layers and insulating layers for insulating the metal layers on a light receiving section and a peripheral circuit section of a substrate. Subsequently, through-wires that pierce through the image sensor wafer are respectively formed for each of the image pickup devices. Thereafter, connection electrodes to other apparatuses are formed for each of the image pickup devices in parts drawn out to a surface opposite to a surface of the image sensor wafer on which the translucent cover glass wafer is stuck in the respective through-wires. Finally, the image sensor wafer is separated into respective chips by dicing or the like for each of the image pickup devices.

The configuration and the manufacturing method of the image pickup apparatus by the WL-CSP explained above are disclosed in, for example, Japanese Patent Application Laid-Open Publication No. 2010-219402.

Conventionally, a configuration for reducing, in order to attain refining of a wire and an increase in speed of a signal, resistance of a wire by using Cu rather than conventionally-used Al in a plurality of metal layers functioning as wiring layers is well known.

In recent years, according to further progress of refining and a reduction in a pitch, in order to prevent a wiring delay due to parasitic capacitance that occurs among a plurality of metal layers, instead of silicon oxide-based films conventionally used in insulating layers, more specifically, a Tetraethyl orthosilicate (TEOS)-CVD film, a Spin-On Dielectrics (SOD) film, and the like, adoption of a low-dielectric insulating film having a lower relative dielectric constant, that is, a film called "Low-k insulating film" is ongoing.

SUMMARY OF THE INVENTION

An image pickup apparatus in an aspect of the present invention includes: a substrate, on a principal plane of which a light receiving section and a peripheral circuit section are formed; a multilayer wiring layer stacked on the principal plane of the substrate, including a plurality of metal layers electrically connected to the light receiving section and the peripheral circuit section and insulating layers for insulating the metal layers, and, in plan view of the principal plane, formed in a size for covering at least the light receiving section and the peripheral circuit section and in an external shape smaller than the substrate; a translucent cover located on the multilayer wiring layer, formed in an external shape larger than the multilayer wiring layer, and formed in a size same as an external shape of the substrate or smaller than the external shape of the substrate; and a side surface sealing member extending from a peripheral section of a surface opposed to the multilayer wiring layer in the translucent cover to the substrate side while having a frame shape, an extending end of the side surface sealing member being water-tightly set in contact with a non-formation region of the multilayer wiring layer on the principal plane of the substrate to thereby protect an outer peripheral side surface of the multilayer wiring layer.

An endoscope in an aspect of the present invention includes an image pickup apparatus including: a substrate, on a principal plane of which a light receiving section and a peripheral circuit section are formed; a multilayer wiring layer stacked on the principal plane of the substrate, including a plurality of metal layers electrically connected to the light receiving section and the peripheral circuit section and insulating layers for insulating the metal layers, and, in plan view of the principal plane, formed in a size for covering at least the light receiving section and the peripheral circuit section and in an external shape smaller than the substrate; a translucent cover located on the multilayer wiring layer, formed in an external shape larger than the multilayer wiring layer, and formed in a size same as an external shape of the substrate or smaller than the external shape of the substrate; and a side surface sealing member extending from a peripheral section of a surface opposed to the multilayer wiring layer in the translucent cover to the substrate side while having a frame shape, an extending end of the side surface sealing member being water-tightly set in contact with a non-formation region of the multilayer wiring layer on the principal plane of the substrate to thereby protect an outer peripheral side surface of the multilayer wiring layer.

DETAILED DESCRIPTION OF THE PREFERRED EMBODIMENT(S)

Embodiments of the present invention are explained below with reference to the drawings. It should be noted that the drawings are schematic and relations between thicknesses and widths of respective members, ratios of the thicknesses of the respective members, and the like are different from real ones. It goes without saying that portions having relations and ratios of dimensions different from one another are included among the drawings.

First Embodiment

Figure 1:
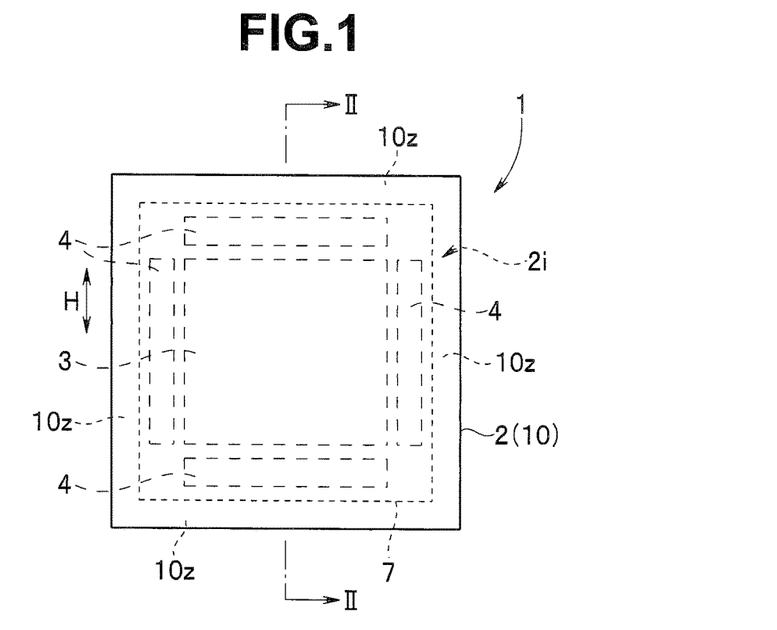
FIG. 1 is a plan view schematically showing a configuration of an image pickup apparatus of a first embodiment.
Figure 2:
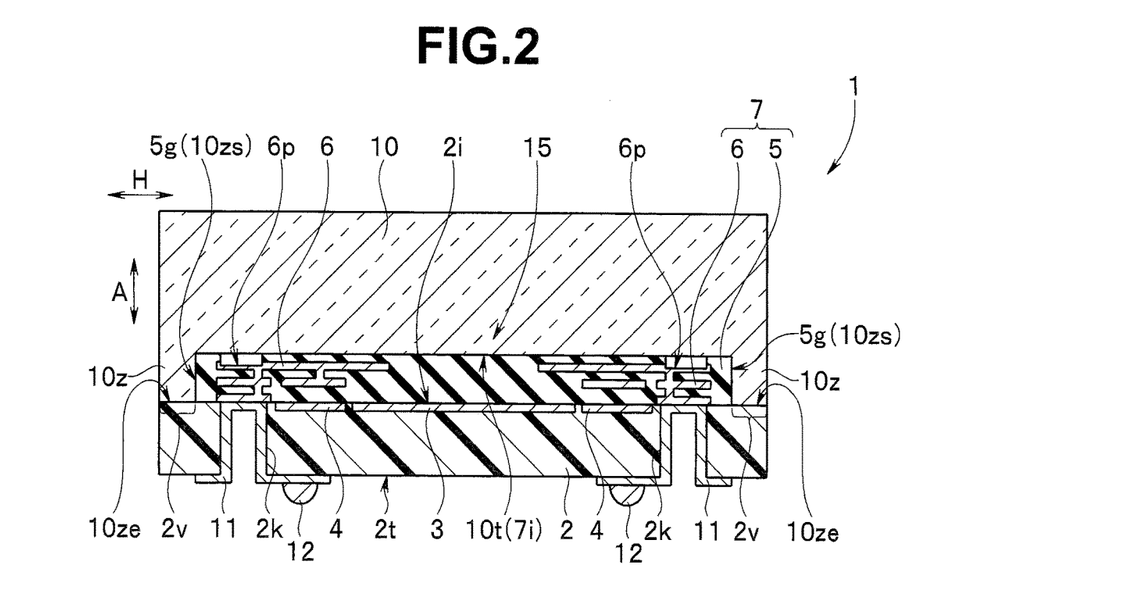
FIG. 2 is a sectional view of the image pickup apparatus taken along line II-II in FIG. 1.

FIG. 1 is a plan view schematically showing a configuration of an image pickup apparatus of the present embodiment. FIG. 2 is a sectional view of the image pickup apparatus taken along line II-II in FIG. 1.

As shown in FIG. 1 and FIG. 2, an image pickup apparatus 1 includes an image pickup device 15, a main part of which is configured from a substrate 2 and a multilayer wiring layer 7.

In the substrate 2, a light receiving section 3 is formed in substantially the center of a first surface 2i, which is a principal plane, and, on the first surface 2i, peripheral circuit sections 4 are formed in peripheral positions in four directions surrounding the light receiving section 3 in a plan view state of the first surface 2i.

Note that examples of the peripheral circuit sections 4 include a shift register, an output amplifier, an A/D converter, and a memory circuit, which may be formed in the peripheral positions in two or three directions among the four directions according to necessity.

The multilayer wiring layer 7 is stacked on the first surface 2i of the substrate 2. As shown in FIG. 2, the multilayer wiring layer 7 is configured from metal layers 6 formed by a plurality of layers electrically connected to the light receiving section 3 and the peripheral circuit sections 4 and insulating layers 5 for insulating the metal layers 6. As shown in FIG. 1, in plan view of the first surface 2i, the multilayer wiring layer 7 is formed in a size for covering at least the light receiving section 3 and the peripheral circuit sections 4 and in an external shape smaller than the substrate 2.

Examples of a material configuring the metal layers 6 include, besides conventionally-used Al, Cu having wiring resistance smaller than wiring-resistance of Al.

As a material configuring the insulating layers 5, besides a conventionally-used $SiO_2$-based film, the Low-k insulating film explained above or the like is used to further reduce interlayer capacitance.

The Low-k insulating film has a relative dielectric constant (k) preferably equal to or lower than 3.9 and more preferably equal to or lower than 2.7.

More specifically, it is desirable to use a fluorine-doped silicon oxide film (SiOF/FSG), a carbon-doped silicon oxide film (SiOC), a hydrogen-containing polysiloxane (HSQ)-based film, a methyl-containing polysiloxane (MSQ)-based film, and an organic (polyimide, parylene, Teflon (registered trademark)) film, and the like and use a porous material and an insulating film of, for example, a form having air gaps.

On a surface (hereinafter referred to as upper surface) 7i on an opposite side of a surface of the multilayer wiring layer 7 in contact with the substrate 2, since the insulating layers 5 opposed to a part of the metal layers 6 are removed, a part of the metal layers 6 is exposed as electrode pads 6p. Note that the electrode pads 6p are used when the image pickup apparatus 1 and an external apparatus are electrically connected.

In the substrate 2, in plan view of the first surface 2i, through-holes 2k piercing through the substrate 2 in a height direction A are formed in regions on outer sides in a width direction H of the peripheral circuit sections 4, more specifically, regions overlapping the metal layers 6.

On the inner circumferential surfaces of the through-holes 2k, through-wires 11 electrically connected to the metal layers 6 via the through-holes 2k are formed. Note that not-shown insulating films are fainted between the through-wires 11 and the substrate 2. The through-wires 11 and the substrate 2 are electrically insulated.

The through-wires 11 are drawn out to a second surface 2t on an opposite side of the first surface 2i of the substrate 2. Back electrodes 12 for connecting the image pickup apparatus 1 to the external apparatus are electrically connected to parts drawn out to the second surface 2t. Consequently, in the configuration, the electrode pads 6p are electrically connected to the back electrodes 12 via the metal layers 6 and the through-wires 11.

Note that wires extending from the electrode pads 6p are not limited to the through-wires 11 connected via the through-holes 2k and may be inner leads 53 of TAB substrates 55 (for both of which, see FIG. 10) explained below electrically connected to the electrode pads 6p.

On the upper surface of the multilayer wiring layer 7, a translucent cover 10 formed in an external shape larger than the multilayer wiring layer 7 and formed in a size same as an external shape of the substrate 2 or smaller than the external shape of the substrate 2 is stuck via a not-shown resin material, for example, an adhesive. Note that the translucent cover is configured from an inorganic material, for example, a glass material.

Further, a frame-like side surface sealing member 10z extending in a convex shape from a surface 10t to the substrate 2 side and formed in an external shape smaller than the translucent cover 10 is fixed in a peripheral section of the surface 10t opposed to the upper surface 7i of the multilayer wiring layer 7 in the translucent cover 10.

Note that, in the present embodiment, the side surface sealing member 10z is formed integrally with the translucent cover 10. In this case, the side surface sealing member 10z is configured from a glass material, which is an inorganic material same as the translucent cover 10.

However, the side surface sealing member 10z may be a separate body bonded to the translucent cover 10. In this case, the side surface sealing member 10z only has to be configured from an inorganic material into which moisture does not permeate, for example, a silicon material.

In the side surface sealing member 10z, at an extending end 10ze, a non-formation region 2v of the multilayer wiring layer 7 on the first surface 2i of the substrate 2, that is, the multilayer wiring layer 7 is formed in an external shape smaller than the substrate 2. Therefore, the side surface sealing member 10z is water-tightly set in contact with the region 2v where the first surface 2i of the substrate 2 is exposed.

Note that the extending end 10ze is bonded to the non-formation region 2v by known anodic bonding. Naturally, the extending end 10ze may be bonded to the non-formation region 2v via an adhesive.

An inner peripheral surface 10zs of the side surface sealing member 10z is stuck to an outer peripheral side surface of the multilayer wiring layer 7, that is, outer peripheral side surfaces 5g of the insulating layers 5 via a resin material, for example, an adhesive. Note that the inner peripheral surface 10zs does not have to be in contact with and bonded to the outer peripheral side surfaces 5g.

Because the extending end 10ze is water-tightly set in contact with the non-formation region 2v, the side surface sealing member 10z is a member that seals the outer peripheral side surfaces 5g from being exposed, that is, protects the outer peripheral side surfaces 5g to thereby prevent moisture from intruding into the multilayer wiring layer 7 from an outside.

Next, a method of manufacturing the image pickup apparatus 1 is briefly explained with reference to FIG. 3 to FIG. 8.

Figure 3:
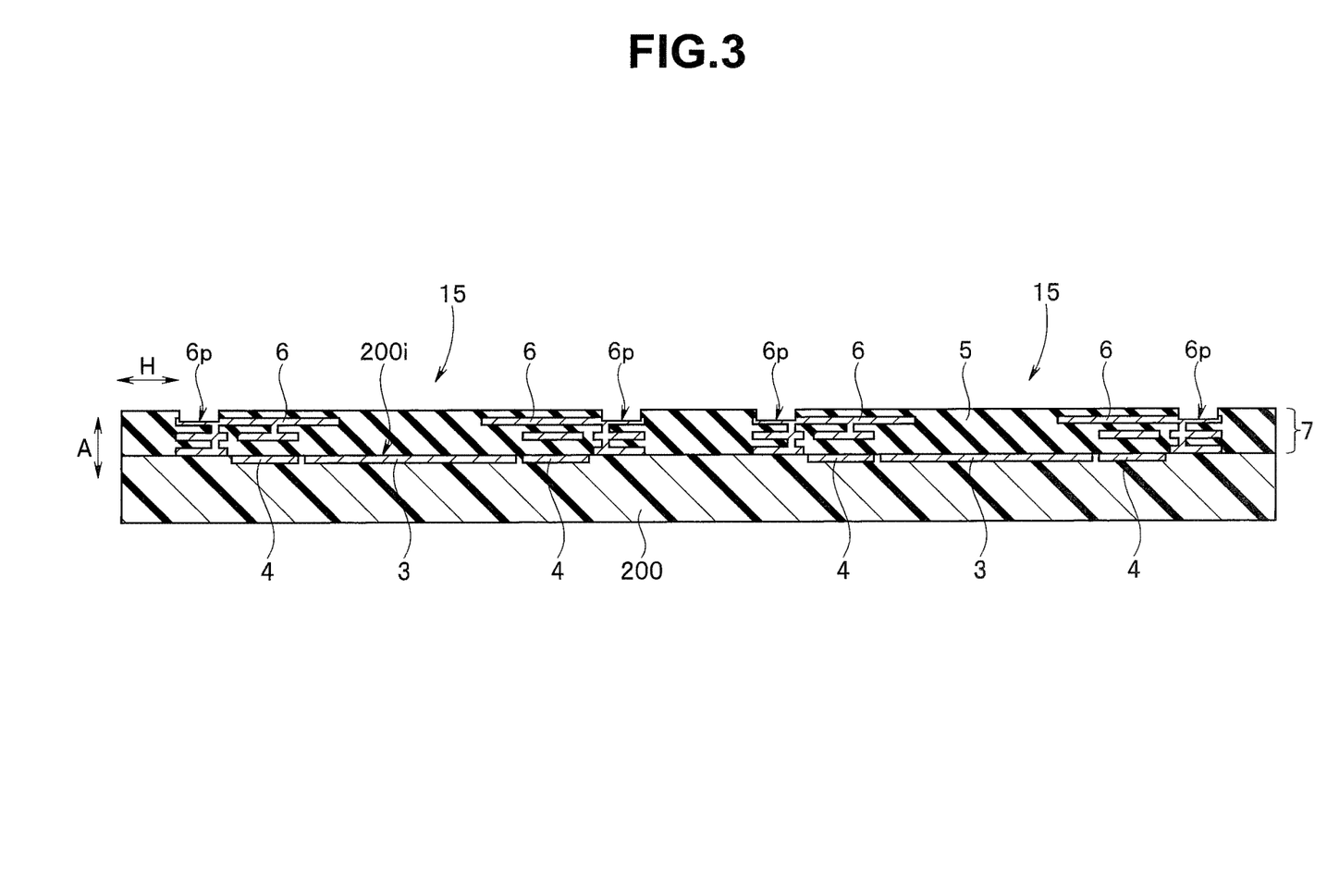
FIG. 3 is a sectional view showing an image sensor wafer on which a light receiving section and peripheral circuit sections are formed for each of image pickup devices.
Figure 4:
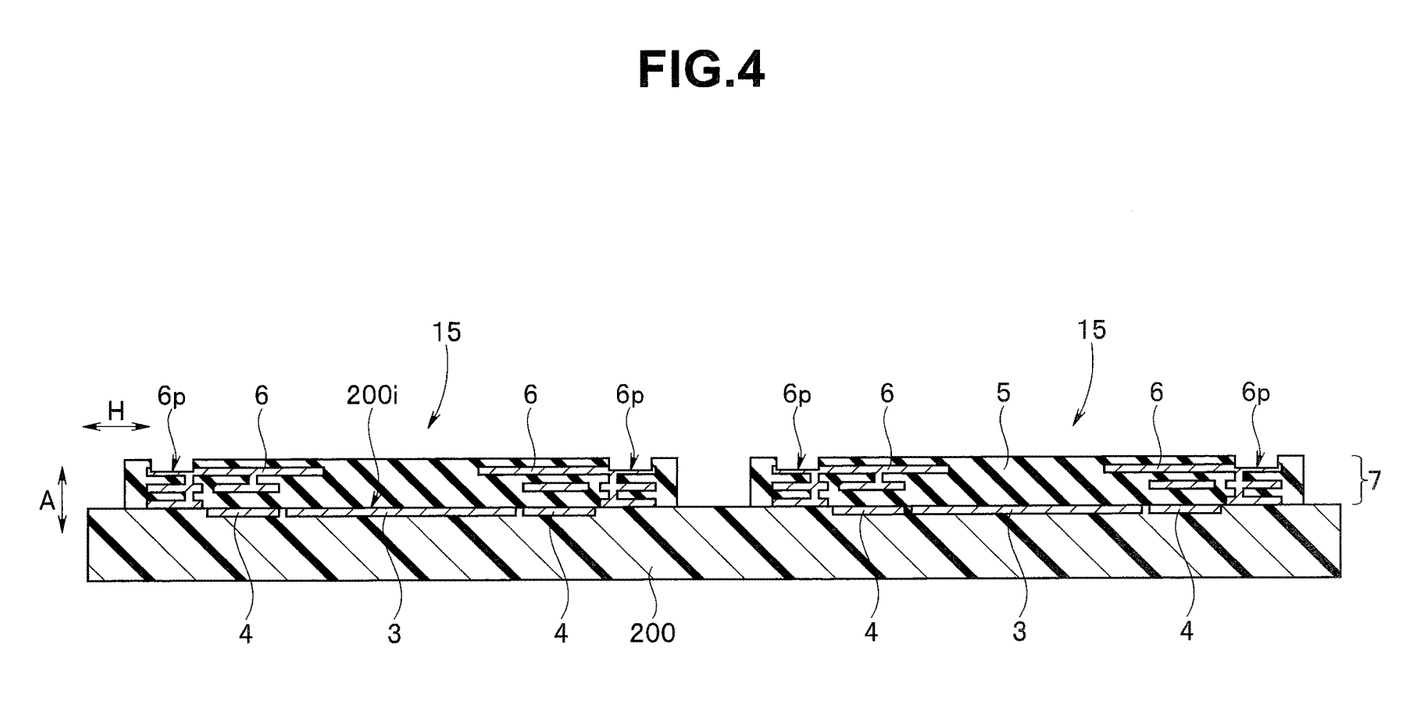
FIG. 4 is a sectional view showing a state in which regions further on outer sides than metal layers are removed for each of the image pickup devices in insulating layers of the image sensor wafer shown in FIG. 3.

FIG. 3 is a sectional view showing an image sensor wafer in which a light receiving section and peripheral circuit sections are formed for each of image pickup devices. FIG. 4 is a sectional view showing a state in which regions further on outer side than metal layers are removed for each of the image pickup devices in insulating layers of the image sensor wafer.

Figure 5:
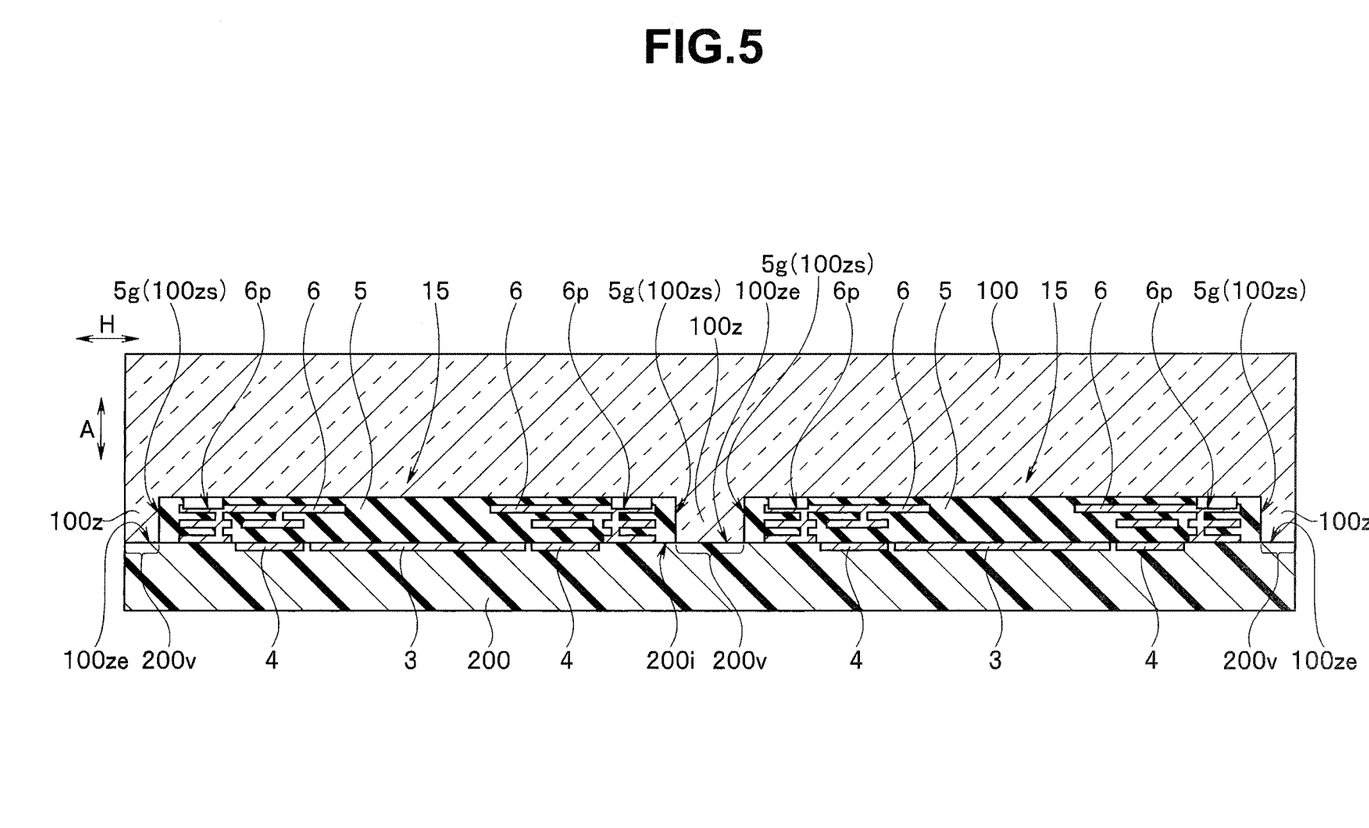
FIG. 5 is a sectional view showing a state in which a translucent cover glass wafer integrally formed with a side surface sealing member is stuck on a principal plane and a multilayer wiring layer of the image sensor wafer shown in FIG. 4.
Figure 6:
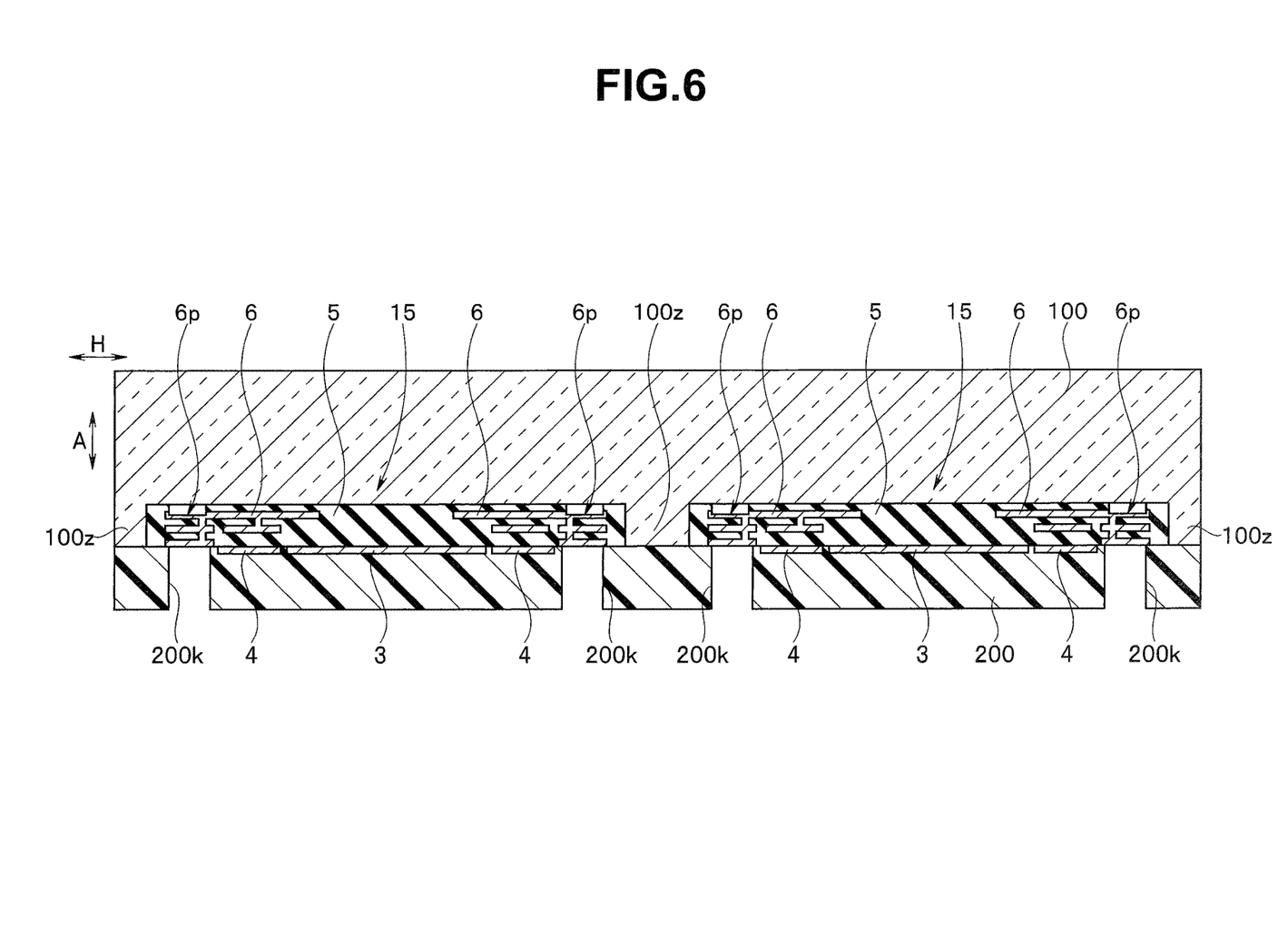
FIG. 6 is a sectional view showing a state in which through-holes are formed for each of the image pickup devices in the image sensor wafer shown in FIG. 5.

FIG. 5 is a sectional view showing a state in which a translucent cover glass wafer integrally formed with a side surface sealing member is stuck on a first surface and a multilayer wiring layer of the image sensor wafer shown in FIG. 4. FIG. 6 is a sectional view showing a state in which through-holes are formed for each of the image pickup devices in the image sensor wafer shown in FIG. 5.

Figure 7:
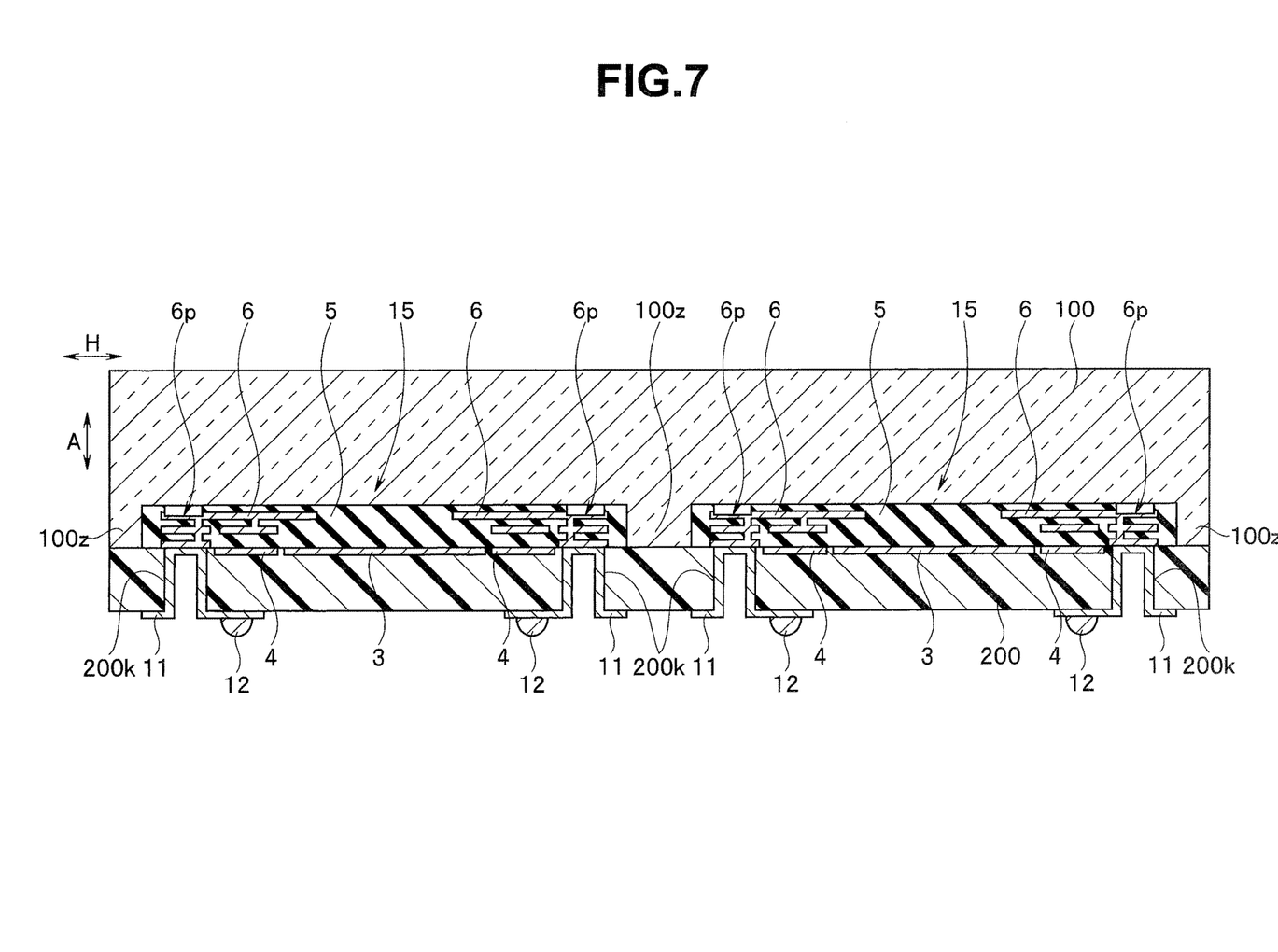
FIG. 7 is a sectional view showing a state in which through-wires are formed in the through-holes formed in the image sensor wafer shown in FIG. 6 and back electrodes are electrically connected to the through-wires.
Figure 8:
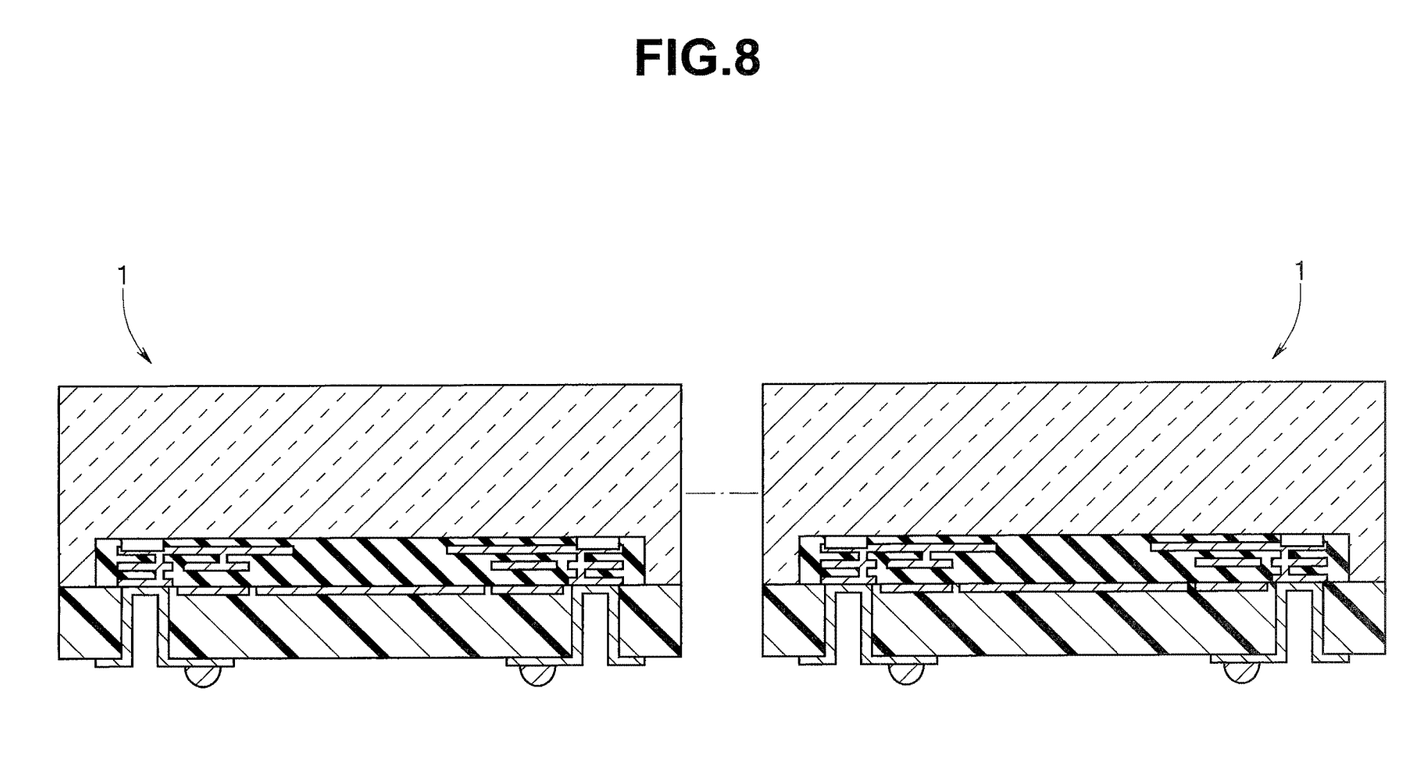
FIG. 8 is a sectional view showing a state in which the translucent cover glass wafer stuck to the image sensor wafer shown in FIG. 7 is divided and respective image pickup apparatuses are formed.

Further, FIG. 7 is a sectional view showing a state in which through-wires are formed in the through-holes formed in the image wafer shown in FIG. 6 and back electrodes are electrically connected to the through-wires. FIG. 8 is a sectional view showing a state in which the translucent cover glass wafer stuck to the image sensor wafer shown in FIG. 7 is divided and respective image pickup apparatuses are formed.

First, as shown in FIG. 3, after the light receiving section 3 and the peripheral circuit sections 4 are respectively formed for each of the image pickup devices 15 on a first surface 200i of an image sensor wafer 200 configured from silicon or the like, the multilayer wiring layer 7 is formed on the first surface 200i.

Subsequently, as shown in FIG. 4, in the insulating layers 5 of the multilayer wiring layer 7, the peripheral circuit sections 4, more specifically, regions further on outer sides than the metal layers 6 are removed in a peripheral shape for each of the image pickup devices 15. Note that the removal of the insulating layers 5 is performed by laser grooving, half-cut dicing by a dicing blade, etching, or the like.

Subsequently, after a translucent cover glass wafer 100 configured from an inorganic material is prepared, the translucent cover glass wafer 100 is etched. Consequently, when the translucent cover glass wafer 100 is stuck on the multilayer wiring layer 7, a frame-like side surface sealing member 100z is formed that fits in parts where the insulating layers 5 are removed in FIG. 4 and is set in contact with parts 200v exposed on the first surface 200i of the image sensor wafer 200 by the removal of the insulating layers 5 and protects the outer peripheral side surfaces 5g of the insulating layers 5 for each of the image pickup devices 15.

Note that, when the side surface sealing member 100z is formed separately from the translucent cover glass wafer 100, the side surface sealing member 100z configured from silicon may be formed by, for example, sticking a silicon wafer configured from an inorganic material to the translucent cover glass wafer 100 and patterning the silicon wafer.

Subsequently, as shown in FIG. 5, the translucent cover glass wafer 100 is stuck on the multilayer wiring layer 7, the side surface sealing member 100z is fit in the parts where the insulating layers 5 are removed in FIG. 4, and an extending end 100ze of the side surface sealing member 100z is water-tightly set in contact with the parts 200v of the first surface 200i and bonded to the parts 200v by the known anodic bonding. Simultaneously with the bonding, an inner peripheral surface 100zs of the side surface sealing member 100z is stuck to the outer peripheral side surfaces 5g of the insulating layer 5 via an adhesive.

Note that, as explained above, when the side surface sealing member 100z is separated from the translucent cover glass wafer 100, the extending end 100ze is stuck to the parts 200v by an adhesive.

Thereafter, as shown in FIG. 6, in the image sensor wafer 200, for each of the image pickup devices 15, in plan view of the first surface 200i, through-holes 200k piercing through the image sensor wafer 200 in the height direction A are formed in regions on outer sides in the width direction H of the peripheral circuit sections 4, more specifically, regions overlapping the metal layers 6.

Subsequently, as shown in FIG. 7, the through-wires 11 are formed in the through-holes 200k and on a second surface 200t of the image sensor wafer 200. The back electrodes 12 electrically connected to the electrode pads 6p via the metal layers 6 and the through-wires 11 are foamed in the parts of the through-wires 11 located on the second surface 200t. Note that not-shown insulating films are formed between the through-wires 11 and the substrate 2 to electrically insulate the through-wires 11 and the substrate 2.

Finally, a structure shown in FIG. 7 is divided by, for example, dicing in positions where the side surface sealing member 100z is formed other than end faces of the image sensor wafer 200 and the translucent cover glass wafer 100, whereby, as shown in FIG. 8, a plurality of the image pickup apparatuses 1 are formed.

In this way, in the present embodiment, the multilayer wiring layer 7 is formed in the external shape smaller than the substrate 2. Consequently, the extending end 10ze of the side surface sealing member 10z is water-tightly set in contact with the non-formation region 2v of the multilayer wiring layer 7 formed on the first surface 2i of the substrate 2, whereby the outer peripheral side surfaces 5g of the insulating layers 5 in the multilayer wiring layer 7 of the substrate 2 are sealed and protected by the side surface sealing member 10z configured from the inorganic material into which moisture does not permeate.

Therefore, since the outer peripheral side surfaces 5g of the insulating layers 5 are protected by the side surface sealing member 10z configured from the inorganic material into which moisture does not permeate, the insulating layers 5 are not exposed to the outside. Therefore, treatment is easy in a manufacturing process. Further, since moisture does not intrude into an inside from the outside, it is possible to prevent corrosion of the metal layers 6.

Note that the effects explained above are particularly effective when the insulating layers 5 are configured from the Low-k insulating film. It is possible to more effectively prevent peeling of the insulating layers 5 and a change in a dielectric constant of the insulating layers 5.

Consequently, it is possible to provide the image pickup apparatus 1 and an endoscope with high reliability by protecting the outer peripheral side surfaces 5g of the insulating layers 5 to thereby prevent damage to the insulating layers 5 and prevent intrusion of moisture via the insulating layers 5 to improve moisture resistance.

Figure 9:
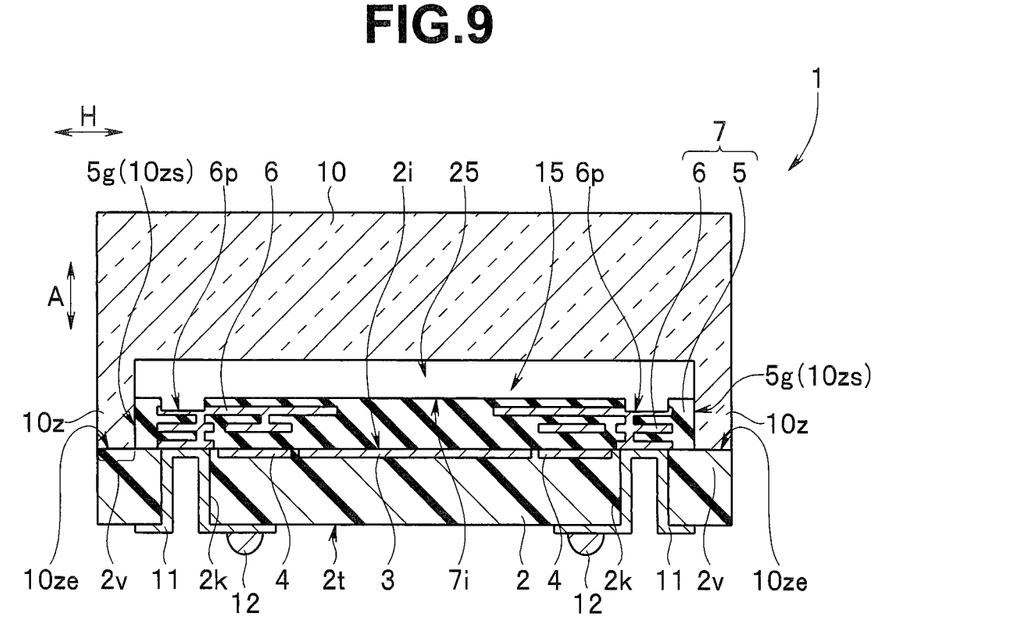
FIG. 9 is a sectional view showing a modification in which a gap is provided between the multilayer wiring layer and a translucent cover shown in FIG. 2.

Note that a modification is explained below with reference to FIG. 9. FIG. 9 is a sectional view showing a modification in which a gap is provided between the multilayer wiring layer shown in FIG. 2 and the translucent cover.

In the present embodiment explained above, the surface 10t of the translucent cover 10 is bonded to the upper surface 7i of the multilayer wiring layer 7.

Without being limited thereto as shown in FIG. 9, a gap called cavity may be formed between the upper surface 7i of the multilayer wiring layer 7 and the surface 10t of the translucent cover 10 by setting height in the height direction A of the side surface sealing member 10z larger than height of the multilayer wiring layer 7. By providing the gap, it is possible to improve a light focusing effect of micro-lenses formed on the light receiving section and improve sensitivity of the image pickup device.

Second Embodiment

Figure 10:
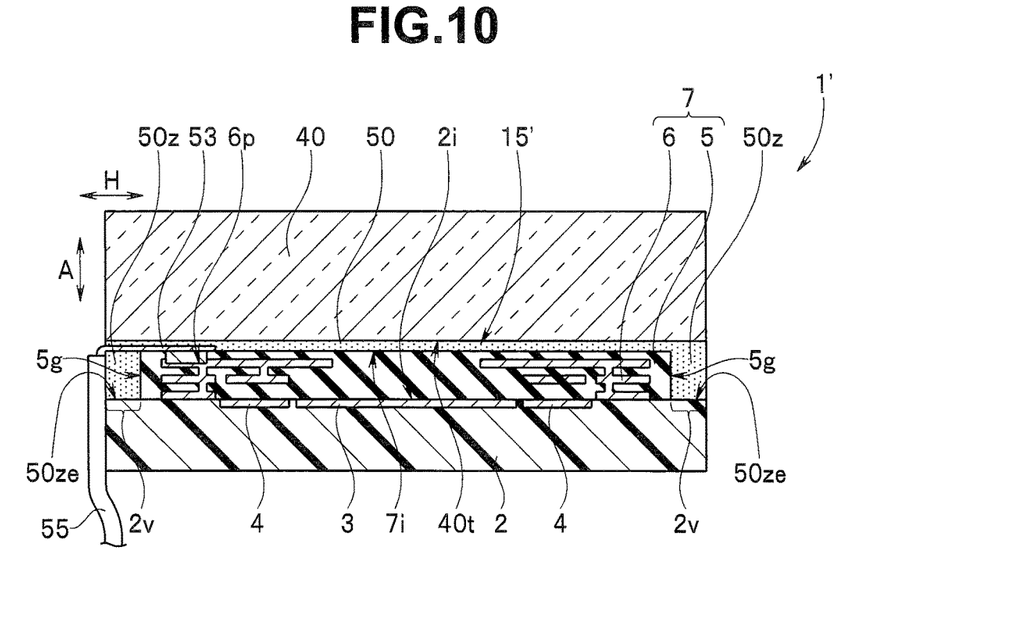
FIG. 10 is a sectional view schematically showing a configuration of an image pickup apparatus of a second embodiment.

FIG. 10 is a sectional view schematically showing a configuration of an image pickup apparatus of the present embodiment.

Compared with the image pickup apparatus of the first embodiment shown in FIG. 2 explained above, the configuration of the image pickup apparatus of the second embodiment is different in that a side surface sealing member is configured from a resin material.

Therefore, only the differences are explained. Components same as the components in the first embodiment are denoted by the same reference numerals and signs and explanation of the components is omitted.

As shown in FIG. 10, in an image pickup apparatus 1' of the present embodiment, a side surface sealing member 50z is configured from the same material as an adhesive 50 configured from a resin material for bonding a surface 40t of a translucent cover 40 over an entire surface of the upper surface 7i of the multilayer wiring layer 7.

Like the side surface sealing member 10z explained above, in the side surface sealing member 50z, the non-formation region 2v of the multilayer wiring layer 7 on the first surface 2i of the substrate 2, that is, the multilayer wiring layer 7 is formed in an external shape smaller than the substrate 2. Consequently, an extending end 50ze is water-tightly set in contact with the region 2v where the first surface 2i of the substrate 2 is exposed. Therefore, a member is configured that prevents moisture from intruding into the multilayer wiring layer 7 from the outside by sealing the outer peripheral side surfaces 5g of the insulating layers 5 to thereby prevent the outer peripheral side surfaces 5g from being exposed, that is, protect the outer peripheral side surfaces 5g.

Note that examples of resin configuring the adhesive 50 include a low moisture permeability material such as fluorine-based resin. The side surface sealing member 50z may be formed separately from the adhesive 50. That is, the side surface sealing member 50z may be formed by a resin material configured from a low moisture permeability material different from the adhesive 50.

In image pickup devices 15' of the present embodiment, distal ends of the inner leads 53 extending from the TAB (tape automated bonding) substrates 55, which are located along outer peripheral side surfaces of the image pickup devices 15', and bent in halfway positions at approximately 90° are electrically connected to the electrode pads 6p. Consequently, the image pickup apparatus 1' is electrically connectable to an external apparatus via the TAB substrates 55.

Note that in the present embodiment, as in the first embodiment explained above, the image pickup apparatus 1' may include a configuration in which the image pickup apparatus 1' is electrically connected to the external apparatus using the through-wires 11.

Note that the other components of the image pickup apparatus 1' are the same as the components of the image pickup apparatus 1 of the first embodiment explained above.

Next, a method of manufacturing the image pickup apparatus 1' explained above is briefly explained.

First, as shown in FIG. 3 explained above, after the light receiving section 3 and the peripheral circuit sections 4 are respectively formed for each of the image pickup devices 15 on the first surface 200i of the image sensor wafer 200 configured from silicon or the like, the multilayer wiring layer 7 is formed on the first surface 200i.

Subsequently, as shown in FIG. 4, in the insulating layers 5 of the multilayer wiring layer 7, regions further on outer sides than the metal layers 6 are removed in a peripheral shape for each of the image pickup devices 15.

Thereafter, in the present embodiment, the image sensor wafer 200 is divided by, for example, dicing in the non-formation region of the multilayer wiring layer 7 other than the end face of the image sensor wafer 200, whereby a plurality of the image pickup devices 15' are formed.

Subsequently, after the distal ends of the inner leads 53 extending from the TAB substrates 55 are electrically respectively connected to the electrode pads 6p of the respective image pickup devices 15', the inner leads 53 are bent and the TAB substrates 55 are located along the outer peripheral side surfaces of the image pickup devices 15'.

Thereafter, the surface 40t of the translucent cover 40 is stuck to the upper surface 7i of the multilayer wiring layer 7 via the adhesive 50.

In this case, the adhesive 50 is fluidized and flows into parts where the insulating layers 5 are removed in FIG. 4. Finally, when the adhesive 50 is hardened, parts of the adhesive 50 flown into the parts where the insulating layers 5 are removed in FIG. 4 change to the side surface sealing member 50z. The extending end 50ze is water-tightly set in contact with the region 2v where the first surface 2i of the substrate 2 is exposed. Consequently, the outer peripheral side surfaces 5g are protected by sealing the outer peripheral side surfaces 5g of the insulating layers 5.

In this way, even if the adhesive 50 for sticking the surface 40t of the translucent cover 40 to the upper surface of the multilayer wiring layer 7 or a resin material different from the adhesive 50 is used for the side surface sealing member 50z, it is possible to obtain effects same as the effects in the first embodiment.

Further, the inner leads 53 can be embedded in the image pickup apparatus 1' making use of fluidity of the resin material. Therefore, it is possible to firmly fix the inner leads.

Figure 11:
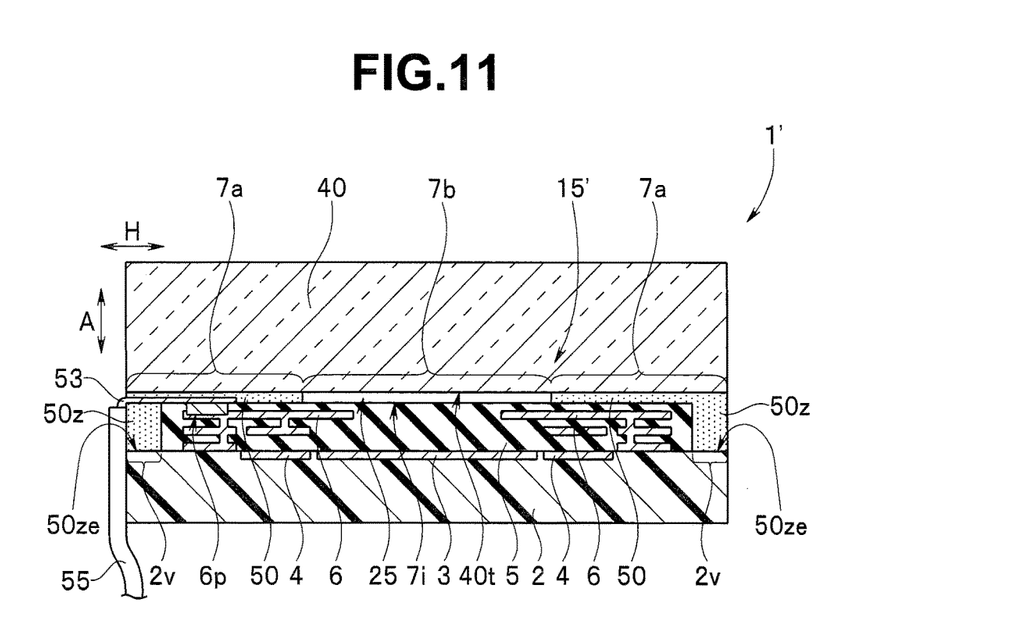
FIG. 11 is a sectional view showing a modification in which a gap is provided in an adhesive that bonds a multilayer wiring layer and a translucent cover shown in FIG. 10.

Note that a modification is explained below with reference to FIG. 11. FIG. 11 is a sectional view showing a modification in which a gap is provided in the adhesive for bonding the multilayer wiring layer and the translucent cover shown in FIG. 10.

In the present embodiment, the surface 40t of the translucent cover 40 is stuck to an entire surface of the upper surface 7i of the multilayer wiring layer 7 via the adhesive.

Without being limited thereto, as shown in FIG. 11, the upper surface 7i of the multilayer wiring layer 7 and the surface 40t of the translucent cover 40 may be stuck via the adhesive 50 applied only to at least a part, more specifically, non-overlapping regions 7a on the light receiving section 3 on the upper surface 7i of the multilayer wiring layer 7. A gap called cavity may be formed between region 7b overlapping the light receiving section 3 in the multilayer wiring layer 7 and the translucent cover 40. By providing the gap, it is possible to improve a light focusing effect of microlenses formed on the light receiving section and improve sensitivity of the image pickup device.

Note that the image pickup apparatuses explained in the first and second embodiments are provided in, for example, an endoscope for medical use or industrial use. Besides, it goes without saying that the image pickup apparatuses may be provided in a capsule endoscope for medical use or may be applied to not only the endoscopes but also a camera-equipped cellular phone and a digital camera.

What is claimed is:

1. An image pickup apparatus comprising:
   a substrate, on a principal plane of which a light receiving section and a peripheral circuit section are formed;
   a multilayer wiring layer stacked on the principal plane of the substrate, the multilayer wiring layer including a plurality of metal layers electrically connected to the light receiving section and to the peripheral circuit section, the multilayer wiring layer further having insulating layers for insulating the metal layers, the multilayer wiring layer being formed to cover at least the light receiving section and the peripheral circuit section in a plan view of the principal plane, and the multilayer wiring layer having an external shape smaller than an external shape of the substrate to define a non-formation region on the principal plane of the substrate where the multilayer wiring layer is not stacked on the principal plane of the substrate;
   a translucent cover, which is a glass substrate, located on the multilayer wiring layer, the translucent cover being formed in an external shape larger than the external shape of the multilayer wiring layer and formed in at least a same size as the external shape of the substrate in the plan view; and
   a side surface sealing member disposed in the non-formation region, the side surface sealing member water-tightly contacting with at least the principal plane of the substrate in the non-formation region to prevent moisture from intruding into the multilayer wiring layer,
   wherein the light receiving section is positioned on the substrate such that light transmitted through the translucent cover is incident on the light receiving section.

2. The image pickup apparatus according to claim 1, further comprising an adhesive for adhering the translucent cover on the multilayer wiring layer, the adhesive being disposed on a part on the multilayer wiring layer or is located apart from the multilayer wiring layer.

3. The image pickup apparatus according to claim 2, wherein the side surface sealing member is configured from an inorganic material.

4. The image pickup apparatus according to claim 3, wherein
   the translucent cover is configured from the inorganic material, and
   the side surface sealing member is formed integrally with the translucent cover.

5. The image pickup apparatus according to claim 2, wherein the side surface sealing member is configured from a resin material.

6. The image pickup apparatus according to claim 5, wherein
   the adhesive comprises the resin material and the translucent cover is adhered on the multilayer wiring layer by the resin material.

7. The image pickup apparatus according to claim 2, wherein
   the translucent cover is located apart from the multilayer wiring layer, and
   the translucent cover having a gap formed between a surface of the multilayer wiring layer and a surface of the translucent cover.

8. The image pickup apparatus according to claim 6, wherein
   the translucent cover is stuck on the multilayer wiring layer by applying the adhesive on the multilayer wiring layer to non-overlapping regions the non-overlapping regions being regions on the multilayer wiring layer that do not overlap with the light receiving section in the plan view, and
   the translucent cover having a gap formed between a surface of the multilayer wiring layer and a surface of the translucent cover, a region overlapping the light receiving section being a region on the multilayer wiring layer that overlaps with the light receiving layer in the plan view.

9. The image pickup apparatus according to claim 1, wherein the insulating layers are configured from a Low-k insulating film.

10. An endoscope comprising the image pickup apparatus according to claim 1.

11. The image pickup apparatus according to claim 1, wherein the side surface sealing member having a frame shape corresponding to an outer peripheral side surface of the multilayer wiring layer.

* * * * *